United States Patent
Friedman et al.

(10) Patent No.: US 10,843,013 B2
(45) Date of Patent: Nov. 24, 2020

(54) LIQUID PRECURSOR COMPOSITIONS AND USES THEREOF FOR A PH-DEPENDANT SUSTAINED RELEASE TREATMENT OF ORAL DISORDERS

(75) Inventors: Michael Friedman, Jerusalem (IL); Doron Steinberg, Jerusalem (IL); Irith Gati, Mevaseret Zion (IL)

(73) Assignee: YISSUM RESEARCH DEVELOPMENT COMPANY OF THE HEWBREW UNIVERSITY OF JERUSALEM LTD., Jerusalem (IL)

(*) Notice: Subject to any disclaimer, the term of this patent is extended or adjusted under 35 U.S.C. 154(b) by 0 days.

(21) Appl. No.: 13/500,394

(22) PCT Filed: Oct. 5, 2010

(86) PCT No.: PCT/IL2010/000808
§ 371 (c)(1),
(2), (4) Date: Jul. 30, 2012

(87) PCT Pub. No.: WO2011/042897
PCT Pub. Date: Apr. 14, 2011

(65) Prior Publication Data
US 2012/0288566 A1    Nov. 15, 2012

Related U.S. Application Data

(60) Provisional application No. 61/248,544, filed on Oct. 5, 2009.

(51) Int. Cl.
| | | |
|---|---|---|
| *A61Q 11/00* | (2006.01) | |
| *A61K 47/32* | (2006.01) | |
| *A61K 47/36* | (2006.01) | |
| *A61K 9/70* | (2006.01) | |
| *A61K 8/49* | (2006.01) | |
| *A61K 8/43* | (2006.01) | |
| *A61K 8/73* | (2006.01) | |
| *A61K 47/38* | (2006.01) | |
| *A61K 9/00* | (2006.01) | |
| *A61K 8/34* | (2006.01) | |
| *A61K 9/08* | (2006.01) | |
| *A61K 8/86* | (2006.01) | |

(52) U.S. Cl.
CPC .............. *A61Q 11/00* (2013.01); *A61K 8/347* (2013.01); *A61K 8/43* (2013.01); *A61K 8/4926* (2013.01); *A61K 8/731* (2013.01); *A61K 8/86* (2013.01); *A61K 9/0063* (2013.01); *A61K 9/08* (2013.01); *A61K 9/7007* (2013.01); *A61K 47/32* (2013.01); *A61K 47/36* (2013.01); *A61K 47/38* (2013.01); *A61K 2800/31* (2013.01); *A61K 2800/594* (2013.01)

(58) Field of Classification Search
CPC ........ A61Q 11/00; A61K 47/38; A61K 47/36; A61K 47/32; A61K 8/347; A61K 9/08; A61K 9/0063; A61K 8/86; A61K 8/731; A61K 8/4926; A61K 8/43; A61K 9/7007; A61K 2800/594; A61K 2800/31
See application file for complete search history.

(56) References Cited

U.S. PATENT DOCUMENTS

| | | | |
|---|---|---|---|
| 5,102,668 A | | 4/1992 | Eichel et al. |
| 5,160,737 A | * | 11/1992 | Friedman et al. ............ 424/401 |
| 6,197,331 B1 | | 3/2001 | Lerner et al. |
| 2006/0120977 A1 | * | 6/2006 | Friedman et al. ............. 424/61 |
| 2007/0190124 A1 | * | 8/2007 | Zhang ................. A61K 9/7015 424/448 |
| 2008/0193524 A1 | * | 8/2008 | Kodipyaka .......... A61K 9/2846 424/463 |

FOREIGN PATENT DOCUMENTS

| | | | |
|---|---|---|---|
| WO | 9915210 A2 | 4/1999 | |
| WO | WO 0030617 | * 11/1999 | .............. A61K 9/14 |

OTHER PUBLICATIONS

Goto J. Microencapsulation, 1986 p. 305.*
Samaranayake acid prod. saliva glucose. J. Oral Pathology & Med. 15, p. 251 (Year: 1986).*
Friedman Sustained-Release Delivery Systems p. 313 (Year: 1990).*
PCT/IL2010/000808 "International Search Report" (dated Oct. 5, 2010).

* cited by examiner

*Primary Examiner* — Matthew P Coughlin
*Assistant Examiner* — Thurman Wheeler
(74) *Attorney, Agent, or Firm* — Browdy and Neimark, PLLC

(57) ABSTRACT

The present invention discloses liquid precursor compositions adapted for application on a hard surface in the oral cavity, comprising at least one therapeutic agent suitable for the treatment of oral disorders, at least one acidic-pH sensitive polymer, at least one hydrophobic polymer, and a pharmaceutically acceptable volatile carrier, wherein a weight ratio between said at least one hydrophobic polymer and said at least one acidic-pH sensitive polymer is larger than 1. The invention also discloses formulations formed of the solidification of these compositions, and methods for treating oral disorders by applying these compositions on hard surfaces in the oral cavity or to be placed in the oral cavity.

10 Claims, 4 Drawing Sheets

Figure 1:
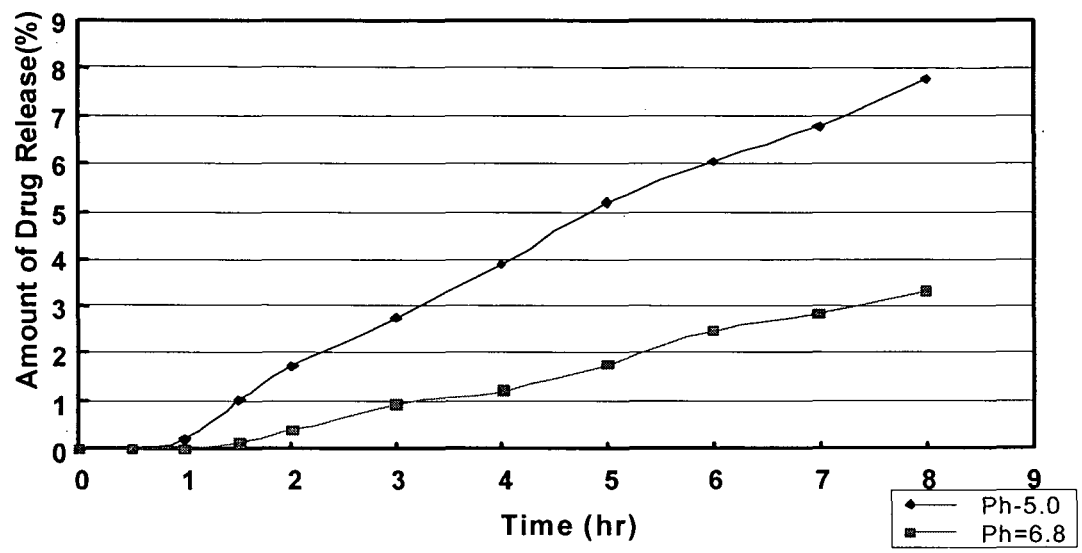

LIQUID PRECURSOR COMPOSITIONS AND USES THEREOF FOR A PH-DEPENDANT SUSTAINED RELEASE TREATMENT OF ORAL DISORDERS

The oral cavity is a very delicate environment. Any changes in the oral hygiene, diet, medicaments or age may result in an oral disorder, such as caries, periodontal diseases, gingivitis, mal odor, tooth staining, bacterial and fungal infections.

In addition, dental hypersensitivity is a frequently encountered problem in dentistry and a very troublesome clinical complaint, which occurs wherever the dentin or cementum of a tooth is exposed due to attrition or abrasion, or when the tooth's fine root surface is exposed due to periodontal disease or any gum associated treatment. For people with hypersensitive teeth everyday stimuli, such as brushing the teeth or consuming cold and/or hot and/or sweet and/or bitter and/or sour foods or drinks, can be painful.

Several therapeutic agents and drug delivery devices are used in an attempt to treat, prevent or ameliorate those disorders: water fluoridation, tablets, gels, drops and tooth pastes are the most common pharmaceutical applications used. The main disadvantage of these drug delivery systems is their low substantivity in the target organ. In particular, the following is noted:

In many cases, a widely used approach is mechanical cleaning methods such as tooth brushing, with or without the use of a variety of toothpaste compositions. Although this method has proved to be fairly successful in treating individuals, it has a high recurrence rate. There is also the problem of motivating people to good oral hygiene habits that they will maintain throughout their lives. In addition, the mentally retarded, handicapped, disabled or hospitalized patients or any subjects with motoric problems are more susceptible to dental disorders due to an inability to properly care of their teeth.

Furthermore, in some cases, such as in the treatment of hypersensitivity, the use of some active ingredients in the toothpaste (for example strontium salts) is disliked by patients due to the unpleasant salty or metallic taste in the mouth.

In some cases, for example for antifungal agents, the active ingredient forms part of mouth rinses, dentifrices, solutions and gels. A main problem with these techniques is that the antifungal drug does not remain in the oral cavity long enough at efficacious levels.

Systemic administration of therapeutic agents, such as antibiotics or antifungal agents has been shown to be a useful method of controlling oral infections; however, discontinuation of therapy will result in the possible return of the potential pathogens. Yet further, when long-term antibiotic therapy is used, it runs the potential dangers of developing resistant strains and superimposed infections.

Sustained release delivery (SRD) systems are pharmaceutical applications in which the active agent is released from the vehicle at a controlled rate.

Several pharmacological advantages stem from the use of SRD: controlled duration and concentrations of the drug in the target site; reduced amount of applied drug and minimal side effects (such as bitter taste, tooth staining, the development of resistant bacterial strains, and the recurrence of oral infections). These advantages in turn result in better clinical improvement and better patient compliance.

Sustained release delivery systems have indeed been reported to be useful in some cases for the local treatment of periodontal disease and in the treatment of plaque prevention in patients wearing orthodontic appliances (see for example, Friedman, M., et al., J. Dent. Res. 64:1319-1321, 1985). In this system, the active ingredient was embedded in an ethyl cellulose polymer to form a film. U.S. Pat. No. 5,330,746 by the present inventors discloses dental liquid precursor compositions for plaque prevention or for treating and/or preventing tooth hypersensitivity, whereas the antibacterial agent or the hypersensitivity agent were embedded in a sustained release carrier, such as a hydrophilic polymer, an acrylic polymer, or a combination of both.

U.S. Pat. No. 5,160,737 by some of the present inventors shows that acrylic polymers can be used as a matrix for sustained release of agents such as cetylpyridium-chloride (CPC).

It appears that during many pathological oral disorders such as those described herein, the pH of the oral cavity decreases from the normal pH of 7.2-6.8 to much lower values. For example, oral bacteria such as the mutans streptococci group in the presence of carbohydrates, reduce oral pH values down to pH=4.0 (Wolinsky L E, Caries and cardiology, In Oral Microbiology and Immunology. Eds; Nisengard and Newman, tend Edition, W.B. Saunders Company Chapter 7 pages 341-359, 1994). In another example, oral fungi, such as *Candida albicans*, reduce oral pH values from 7.5 to 3.8 over a 48 hours fermentation period (Samaranayake et al.: *Growth and acid production of Candida species in human saliva supplemented with glucose*. J. Oral Pathol. 1986 May; 15(5):251-4).

In addition, biofilm formation, which is associated with the drop of pH, is also associated with other oral disorders such as hypersensitive teeth and tooth staining and oral ulceration.

WO 2010/0264333 discloses a device (such as a stent) comprising a body structure, having one or more surfaces which are composed of a pH sensitive layer, that has a changing water solubility at a pH trigger. This device was used to prevent infection when the physiological pH around the device changed, for example due to bacterial infection.

The inventors have now successfully developed a sustained release formulation which increases the release rate at acidic pH, thereby releasing larger amounts of the therapeutic agent when needed—i.e when there is a disorder associated with a reduction in pH, or when the condition deteriorates (evidenced by decreased pH); while at times of remission the release rate will return to the basal release rate.

In addition, it has been shown that acidic conditions are preferable for administration of some drugs in the oral cavity. For example, acidulated fluoride formulations were shown to have an advantage in fluoride penetration, incorporation into caries lesion (Murakami et al., Arch Oral Biol. 2009 November; 54(11):997-1001. Epub 2009 Sep. 1. Effect of fluoride varnish and gel on dental erosion in primary and permanent teeth). The pH sensitive sustained release of a drug (such as fluoride) only at a low pH values, has an enhanced bio-availability and hence pharmacological advantages.

The proposed system is unique in that it has a "built-in" pH sensor that increases the release rate at acidic pH.

In particular, the present invention describes a liquid precursor composition adapted for application on a hard surface in the oral cavity, comprising:
  a) at least one therapeutic agent suitable for the treatment of oral disorders,
  b) at least one acidic-pH sensitive polymer, c) at least one hydrophobic polymer, and
d) a pharmaceutically acceptable volatile carrier,
wherein a weight ratio between the at least one hydrophobic polymer and the at least one acidic-pH sensitive polymer is larger than 1.

The term "liquid" refers to a composition which is fluid at room temperature when present in the vessel.

The term "liquid precursor" means that while the composition of the invention is initially liquid, upon application to a hard surface it solidifies (mainly due to evaporation of the pharmaceutically acceptable volatile carrier or solvent).

The solvent (at times referred to as "carrier") is usually a biocompatible and volatile (at body temperature) solvent.

The carrier suitable to be used as part of the liquid precursor composition of the present invention, should be capable of evaporating under conditions normally present in the oral cavity, optionally capable of evaporation under application of active drying conditions (such as under heat air flow).

Preferably, the carrier is an alcohol or a combination of alcohol and water (a hydro-alcoholic or alcoholic solvent).

More preferably, the carrier is selected from the group consisting of ethyl alcohol or a combination of ethyl alcohol and water or any other solvent that is biocompatible and not toxic.

The term "adapted for application to a hard surface in the oral cavity" refers to the fact that the liquid precursor composition is to be applied (by brushing, dipping, spraying etc) on hard surfaces and is not intended to be applied on the soft surfaces of the oral cavity such as the gums, the tongue, the mouth roof etc. However, it should be clarified that as the therapeutic agents are dispersed gradually into the oral cavity they may also be dispersed in adjacent areas to the hard surfaces, such as soft tissues and gums.

The term "hard surfaces in the oral cavity" includes, but is not limited to teeth or devices that are placed in the mouth such as dentures, implants, orthodontic appliances, retainers, mouth guards, trays or any other potential mouth devices or appliances that are placed inside the mouth.

The term "acidic-pH sensitive polymer" refers to a biocompatible polymer that increases its degradation at acidic pH. The term "acidic pH" as used herein refers to the pH in the oral cavity decreasing below the decreases from the normal pH of 7.2-6.8. More preferably, the acidic-pH sensitive polymer would have an enhanced degradation at about or below pH 6.0.

An example of an acidic pH sensitive polymer is dimethylaminoethyl methacrylate copolymer (Eudragit E). Other acrylate polymers of the Eudragit family and or other polymers containing primary, secondary or tertiary amine groups may be used for this purpose.

The term "hydrophobic polymer" refers to a biocompatible polymer having hydrophobic properties, which is further non-soluble in oral cavity environment. In particular, the hydrophobic polymer should be insoluble in the saliva.

Non-limiting examples of hydrophobic polymers include, but are not limited to the following polymers, as well as their cross-linked versions e.g. aldehydes or polar compounds) and chemical derivatives: copolymer hydrogels of hydroxymethyl methacrylate (HEMA) and methylmethacrylate (MMA), Ethyl cellulose (EC), Silicone rubber, polyethylene, poly(ethylene oxide), poly(acrylic acid), polylactic acid, polymethylmethacrylate, poly(methyl vinyl ether co-maleic anhydride), poly(hydroxyethylmethacrylate), polyvinyl chloride, polyurethane, polyvinyl acetate, cellulose nitrate, karya gum, ethylvinyl acetate, polystyrene, polyamide and proteins.

Preferably, the hydrophobic polymer is selected from copolymer hydrogels of hydroxymethyl methacrylate (HEMA) and methylmethacrylate (MMA), Ethyl cellulose (EC), poly(acrylic acid), poly(methyl vinyl ether co-maleic anhydride), poly(ethylene oxide), karya gum, poly(hydroxyethylmethacrylate), Silicone rubber, polyethylene, polylactic acid, polymethylmethacrylate, polyvinyl chloride, polyvinyl acetate, and polyurethane.

More Preferably, the at least one hydrophobic polymer is selected from: cross linked polymers and derivatives of polymers such as Ethyl cellulose, Silicone rubber, polyethylene, polylactic acid, polymethylmethacrylate, polyvinyl chloride, polyurethane.

In a preferred embodiment of the present invention, the composition comprises Ethyl Cellulose as the hydrophobic polymer and Eudragit E as the acidic pH sensitive polymer.

Generally, the range of the hydrophobic polymer would be from about 30% to about 80%, the pH sensitive polymer ranging from about 10% to about 30%, and the active agent ranging from about 5% to about 40%, all of these in the dry film.

However, in order to achieve the beneficial properties of the present composition, it is important that the ratio between the hydrophobic polymer and the acidic-pH sensitive polymer is kept higher than 1. This will ensure that upon solidification of the liquid precursor composition, the hydrophobic polymer shall form the matrix and the acidic-pH sensitive polymer shall be the component embedded in the hydrophobic matrix.

Typically the ratio between the hydrophobic polymer and the "pH sensitive" polymer (such as Eudragit E) is from about 5:1 to about 1.5:1, yet further preferably from about 3:1 to about 2:1.

It is important to note that the term weight ratio between the hydrophobic polymer and the pH sensitive polymer is the same in the liquid precursor composition, and in the dry film.

The term "oral disorders" includes any oral-related conditions and disorders including conditions that are directly related and associated with oral biofilms, dental and periodontal diseases (such as plaque, dental caries, gingivitis, periodontal diseases, root canal infections, tooth extractions, tooth hypersensitivity, viral infections, xerostomia, burning mouth, ulcers, candidiasis, tumours, aphthous, ulceration, absecsss, stomatitis, halitosis, dry mouth, salivary gland disfunction and including dental esthetics (tooth whitening).

The term "therapeutic agents suitable for the treatment of oral disorders" refers to agents which are intended to prevent, treat, ameliorate, or diminish altogether, any of the oral disorders described hereinabove.

In particular the therapeutic agent is selected from an antibiotic agent, an antibacterial agent, an antiseptic agent, an antifungal agent, an anti-viral agent, a bone and/or tissue growth factor agent, an anti-tumor agent, an anti-inflammatory agent, an anti mal-odor agent, a tooth whitening agent, a bleaching agent, a dental hypersensitivity agent, a plaque treatment agent, dry mouth treatment agent, a biofilm treatment agent, a caries treatment agent, a periodontal diseases treatment agent, a gingivitis treatment agent, a tooth staining treatment agent, anaphthous or ulcer treatment agent, an anti protozoa agent and a Stomatitis agent.

Examples of antibiotic agents include, but are not limited to tetracycline derivatives, penicillin derivatives, erythromycin derivatives, cephalosporin derivatives, Lindomycin derivatives and glycopeptides derivatives.

The term "antibacterial agent" includes any agent capable of killing bacteria.

Examples of an antiseptic agents, include, but are not limited to bacteriocidal quaternary ammonium salt such as cetylpyridinium chloride or benzalkonium chloride or chlorhexidine, or triclosan, or phenols derivatives, or antiseptic volatile oils, herbal antiseptics or other bactericidal agent such as camphorated p-Chlorophenol (CPK).

Examples of antifungal agents include, but are not limited to polyenes, Nystatin, amphotericin, imidazoles, clotrimazole, moconazole, ketonazole, triazoles, fluconazole and itraconazole. In the context of the present invention, the term "antifungal agents" also includes Stomatitis agents.

Examples of anti-viral agents include, but are not limited to acyclovir, amamatadine, diolamosine, famciclovir, foscaruet, gamciclovir, ribavirin, rimantadine, stavudine, zalcitabine, and zioloudine.

Examples of bone and/or tissue growth factor agents include, but are not limited to Bone Morphogenetic Proteins (BMPs), cytokines, IGF and FGF.

Examples of anti-inflammatory agents include, but are not limited to Steroidal and non-steroidal anti-inflammatory agents.

Examples of anti mal-odor agents include, but are not limited to those who act as antibacterial/antiseptic agents or anti enzymatic agents.

Examples of tooth whitening agent, bleaching agents and tooth staining treatment agents include, but are not limited to peroxide agents, carbamide per oxide, hydrogen per oxide.

Examples of dental hypersensitivity agents include, but are not limited to strontium salts (such as strontium chloride or strontium titrate), potassium salts (such as potassium chloride, potassium hydrogen tartrate, or potassium nitrate), fluoride salts (such as stannous fluoride), antimony or oxylates (such as potassium hydrogen oxylates) and may also include amino acids and peptides.

Examples of plaque treatment agents include, but are not limited to antibacterial/antiseptic agents, anti-biofilm agents, Examples of biofilm treatment agents include, but are not limited to antibacterial agents below the minimal inhibitory concentration; herbal extracts e.g. garlic, furanones, homo serine lacton analogues, quorum sensing inhibitors, surfactants and hydrophilic agents.

Examples of caries treatment agents include, but are not limited to such as fluorides compounds e.g. Sodium, amine, stannous, phosphate.

Examples of periodontal diseases treatment agents include, but are not limited to antibiotics, antibacterial, anti inflammatory agents, growth hormones and vasoconstrictors.

Examples of gingivitis treatment agents include, but are not limited to antibacterial antiseptics agents.

Examples of aphthous or ulcer treatment agents include, but are not limited to tetracylcines, minocyclines, triamcinolone, dexamethasone, thalidomide, amlexanox, lidocaine, zinc salts, lysine, vitamins as B complex and C.

Examples of dry mouth treatment agents include, but are not limited to glucose oxidase, menthol, peppermint, lemon, and citric acid, lactoferrin, lactoperoxidase, lysozyme and pilocarpine.

According to specific preferred embodiments, as can be seen in the Examples below, the therapeutic agent is an antibacterial agent and/or an antifungal agent.

More specifically, the therapeutic agent is selected from triclosane, chlorhexidine-diacetate (CHX), clotrimazole and cetylpyridium-chloride (CPC).

The composition of the invention may additionally contain any number of biocompatible additives. These may include, but are not limited to, a plasticizer (such as polyethylene glycol, dibutyl phthalate glycerol or Triacetine), a taste denoting or taste masking agent, such as peppermint, menthol, sugar substitutes volatile extracts, and thickeners such as hydroxyl propyl cellulose, hydroxy propyl methyl cellulose.

The liquid precursor composition described herein is capable of forming upon solidification thereof a matrix made of at least one hydrophobic polymer, having embedded within the at least one acidic-pH sensitive polymer and the at least one therapeutic agent.

The solidification of the liquid precursor of the invention into a solid matrix film can take place naturally by allowing the solvent to evaporate or can be facilitated by applying gentle heated air flow to the mouth.

The obtained matrix, formed by the solidification of the liquid precursor composition, forms a sustained release formulation suitable for the treatment of a variety of oral disorders.

Thus, according to another aspect of the invention, there is provided a sustained release formulation comprising a matrix made of at least one hydrophobic polymer, having embedded within at least one acidic-pH sensitive polymer and at least one therapeutic agent suitable for the treatment of oral disorders, such that the weight ratio between the at least one hydrophobic polymer and the at least one acidic-pH sensitive polymer is larger than 1.

As detailed hereinabove, preferably this ratio ranges from about 5:1 to about 1.5:1, yet further preferably from about 3:1 to about 2:1.

The formulation of the invention can take a number of forms, such as a film, a gel, a foam, a varnish, a dosage meter spray, and a part of a tooth paste or a cartridge within a toothbrush.

After being applied on the hard surface of the oral cavity, it forms a very thin coating on the hard surface onto which it has solidified, this layer ranging from a few microns to a few hundred microns. Preferably, the coating thickness should range from about 30 microns to about 150 microns.

The term "sustained release formulation"—refers to a formulation (in the case in a solid form) that allows an active agent contained therein to transfer to the oral cavity over a prolonged period of time, typically of at least one day.

The sustained release properties of the formulations of the invention are maintained even at these thin coatings, ranging from As the release rate varies with the thickness of the SRD coating it can range from hours to days pending the thickness and the environments as noted hereinabove. The liquid precursor compositions of the present invention are composed of enough hydrophobic polymer, compared to the acidic-pH sensitive polymer (namely that the weight ratio between them is larger than 1), to enable the formation of a hydrophobic matrix in which the pH-sensitive polymer and the therapeutic agent, are embedded.

This matrix is then capable of keeping its sustained release properties on the hard surface in the oral cavity, for hours and days, even at relatively thin coatings pending on the above ratio and the environment and location in the oral cavity (for example, orthodontic appliances and dentures).

Typically, for coatings ranging from 30 microns to 150 microns, the rate of release would range from 3 to 12 hours respectfully.

However, pending on the surface on which the composition is applied, the thickness and the location in the oral cavity, the release rated can be tailored to be at least 3 days.

When the pH is neutral, the formulation of the invention maintains a graduate slow release rate of the therapeutic agent. As explained hereinabove, when dental pathologies or oral disorders develop (for example when bacterial infection effects the oral cavity), a pH decrease to about or below pH 6.0 occurs. In the acidic pH environment formed in the oral cavity, the acidic pH sensitive polymer (for example Eudragit E) is degraded, thereby increasing the release rate of the therapeutic agent from the matrix in which it is also embedded. It should be noted that even at extremely acidic pH not all of the therapeutic agent will be released at once (at a "burst") due to the constant degradation rate of the hydrophobic polymer. The faster release rate of the therapeutic agent will continue until the pH increases again due to the cease of the pathological condition (for examples due to cease of the bacterial infection). This "sensor" effect is far better than a classic sustained release delivery system, in which the release is by a constant profile, regardless of the environmental feedback.

Typically, the formulation in the solid form is resistant to some degree to erosion caused by normal activities such as eating, drinking, brushing teeth etc. It should be emphasized that according to the invention the release rate is not constant but changes in response to the changes in the environment, in particular due to pH changes. The lower the pH (indicative of the presence/deterioration of a disease or a disorder), the faster is the release rate and vise versa—making the release dependent on the severity/existence of the condition or the disorder.

Given these advantages, namely the ability to "sense" oral disorders associated with low pH, the sustained and prolonged release of the therapeutic agent, and the sensitivity of the system to the success of the treatment (and rising of the pH), the formulations described herein are especially suitable for the treatment of oral disorders and conditions.

Thus, according to yet another aspect of the invention, there is provided a method for treating, preventing, ameliorating or eliminating altogether at least one oral disorder, this method comprising topically applying the liquid precursor compositions of the invention to a hard surface in the oral cavity, or to a surface that is intended to be placed in the oral cavity, and allowing the composition to solidify on this surface, thereby forming a film.

The hard surface may therefore be teeth, dentures, retainers, implants, mouth guards, retainers and orthodontic appliances. It may also be any tube or airway appliances or devices inserted into the body via the oral cavity, such as feeding tubes, air ventilation tubes, air tubes and suction tubes.

The term "film" includes both a coating (or coat) and a varnish.

This method of treatment can be affected by being applied into inter-proximal sites, in periodontal pockets, or into tooth root canals It can be applied by brushing, immersing, soaking, spraying on a relevant part of the teeth, oral tissues implants, or any oral appliances or devices for dental or non dental use, as detailed hereinabove.

In one specific embodiment, the liquid precursor compositions of the invention are applied on a dental or oral device, either in or outside of the oral cavity.

Thus, according to another aspect of the invention, there is provided a method for applying on any device to be placed in the mouth, such as dentures, retainers, implants, etc, the above liquid precursor composition of the invention wherein the therapeutic agent is an anti infective (anti bacterial, antiviral, anti protozoa, anti fungal) agent and allowing the liquid composition to solidify, thereby forming a film for sustained release. The application may be by applying the composition to the dentures (by brush, spray etc) or by immersing the denture in the liquid precursor composition of the invention.

The liquid precursor composition and the method of the invention are applicable for human or veterinary use.

EXPERIMENTAL

Materials and Methods
Active Agents
Chlorhexidine-Diacetate (CHX), Cetylpyridinium-Chloride (CPC), Clotrimazole and Triclosane were all obtained from Sigma-Aldrich, St. Louis, USA.
Excipients
Eudragit E PO (Rohm Gmbh, Germany)
Sodium Layryl Sulfate (SLS) (Riedel de Haen, Sigma-Aldrich Gmbh, Germany)
Ethylcellulose—(EC) (Ethocel Premium N 100, Dow Chemical Company Russelville, USA)
Ethanol (J. T. Baker Deventer Holland)
Polyethylenglycol 400(PEG 400) (Schuchardt Hohenbrunn Germany)
Sodium acetate 3 hydrate
1-Heptanesulfonic acid sodium salt (J. T. Baker NJ USA)
Additional Ingredients
Trizma Base (2-amino-2-(hydroxymethyl)-1,3-propanediol)-(Sigma-Aldrich, St. Louis, USA)
Phosphate buffer USP pH=6.8
Phosphate buffer USP pH=5.0

Example 1: Preparation of pH Sensitive Liquid Precursor Compositions Containing Clotrimazole, and Applications Thereof I. Preparation of Liquid Precursor Composition:
PEG400 was weighted into the ethanol. Then, the dry powders of the hydrophobic polymer (Ethyl Cellulose) and the ph-sensitive polymer (Eudragit-E) were slowly added as dry powders to ethanol, and vigorously stirred for about 30 minutes until complete dissolution. Then, the clotrimazole (active agent) was added while continuously stirring.

II. Preparation of Film from the Liquid Precursor Composition:
The liquid precursor composition obtained in part I was poured (15 ml) on Teflon dishes (10.5 cm diameter) in a drying room and dried for about 4 hours. The obtained film was 0.230 mm thick.

Table 1 below shows the clotrimazole sample prepared, showing its composition both in the dry film and in the liquid precursor composition.

TABLE 1

| Formulation | Ingredient | % weight in dry film | % weight in liquid precursor composition |
|---|---|---|---|
| Clotrimazole-1 | Clotrimazole | 52.18 | 5.303 |
|  | Ethyl Cellulose (EC) | 39.13 | 3.98 |
|  | PEG 400 | 4.98 | 0.508 |
|  | Eudragit E | 17.99 | 1.834 |
|  | Ethanol |  | 88.38 |

III. Determining the Release Rate of Clotrimazole from the Film of Part II:

The released clotrimazole concentration was determined by HPLC, using a calibrated graph of known clotrimazole concentrations, as follows, based on Peter de Bruijn et al., 2001 (Liquid chromatographic determination of Ketoconazole, a potent inhibitor of CYP3A-mediated metabolism, Journal of Chromatography B, 753 (2001) 395-400):

A 100 microliter sample was automatically injected into the HPLC(HP 1090 model), equipped with an Inertsil ODS-80A column (5 um 150×4.6 mm GL Science, Tokyo, Japan), and protected by a MetaGuard 4.6 mm Inertsil ODS-3 column (5 um).

The running buffer was a mixture of water, acetonitrile, THF, Triethylamine and AmmoniumHydroxide at a ratio of: 45:50.2:2.5:0.1:0.1 at a pH of 6.0. The flow rate was 1 ml/minute.

The UV absorption was measured at a 206 nm wavelength according to a reference curve Release Rate Experiment:

Determining the clotrimazole release rate from the films was conducted by first placing the films in 350 ml glass vessels, containing Trizma base buffer (50 mM) with 0.2% SLS (sodium lauryl sulphate) at pH=5.0 and 6.8 and 50 cpm, at 37° C.

Then, 1 cc samples were taken from the glass vessels at pre-determined intervals (each hour from 1 to 8 hrs). The released clotrimazole concentration was measured spectrophotometrically at 206 nm (Uvikon 933: Kontron Instruments). The concentration of the CHX was calculated according to a reference curve.

FIG. 1 shows the clotrimazole release rate (as % of the initial amount in film) with time (1-8 hours), for two different pHs: 5.0 and 6.8. As is clear from the figure, the release rate at pH 5.0 was much faster than at pH 6.8

Figure 2:
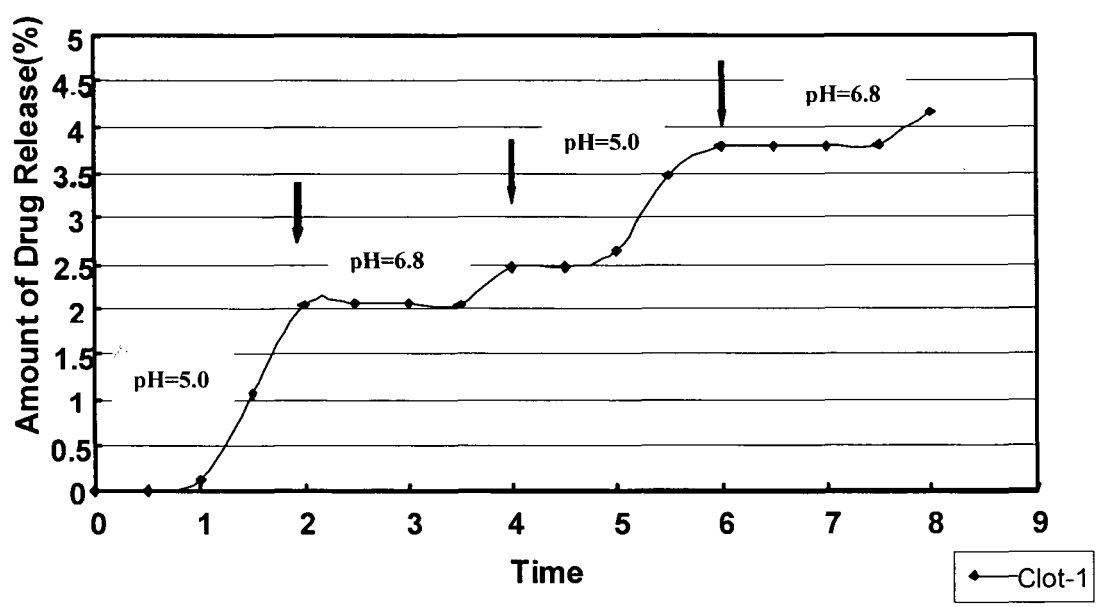

In a different experiment, the films were kept at a pH 5.0 buffer for 2 hours, then kept at a pH 6.8 buffer for 2 hours, then at a pH 5.0 buffer for 2 hours and again at a pH 6.8 buffer for 2 hours. Samples were taken at similar intervals. The results are shown in FIG. 2, which shows the clotrimazole release rate (as % of the initial amount in film) with time (1-8 hours), for this pH change profile. It again demonstrates that pH of 6.8 retards the rate of release from the pH sensitive SRD.

Example 2: Preparation of pH Sensitive Liquid Precursor Compositions Containing Chlorhexidine-Diacetate (CHX), and Applications Thereof I. Preparation of Liquid Precursor Composition:

The liquid precursor composition was prepared as described in Example 1 (part I), replacing the clotrimazole by chlorhexidine-diacetate (CHX).

II. Preparation of Film from the Liquid Precursor Composition:

The liquid precursor composition obtained in part I was poured (21 ml) on Teflon dishes (10.5 cm diameter) in a drying room (37° C.) and dried for about 4 hours. The obtained film was 0.120 mm thick.

Table 2 below shows the CHX sample prepared, showing its composition both in the dry film and in the liquid precursor composition.

TABLE 2

| Formulation | Ingredient | % weight in dry film | % weight in liquid precursor composition |
|---|---|---|---|
| CHX-1 | CHX | 47.4 | 4.5 |
| | Ethyl Cellulose (EC) | 32.6 | 3.1 |
| | PEG 400 | 5.3 | 0.5 |
| | Eudragit E PO | 14.7 | 1.4 |
| | Ethanol | | 90.5 |

III. Determining the Release Rate of CHX from the Film of Part II:

The released CHX concentration was determined using HPLC, using a calibrated graph of known CHX concentrations, as follows based on Y. W. Francis Lam et al, 1993 (Sensitive high performance liquid chromatographic assay for the determination of chlorhexidine in saliva, Journal of ChromatogrPHY, 612 (1993) 166-171):

A 50 microliter sample was automatically injected into the HPLC(HP 1090 model), equipped with an Inertsil ODS-80A column (5 um 150×4.6 mm GL Science, Tokyo, Japan), and protected by a MetaGuard 4.6 mm Inertsil ODS-3 column (5 um).

The running buffer was 40% ACN, 60% 0.05M Sodium Acetate, 0.05M heptane sulfonic acid pH=5.0.

The flow rate was 1 ml/minute.

The UV absorption was measured at a 260 nm wavelength and the CHX concentration was determined by a reference curve.

Release Rate Experiment:

Determining the CHX release rate from the films was conducted by first placing the films in 100 ml glass vessels, containing phosphate buffer at pH=5.0 and 6.8 and 50 cpm, at 37° C.

Then, 1 cc samples were taken from the glass vessels at pre-determined intervals (each hour from 1 to 8 hrs).

Figure 3:
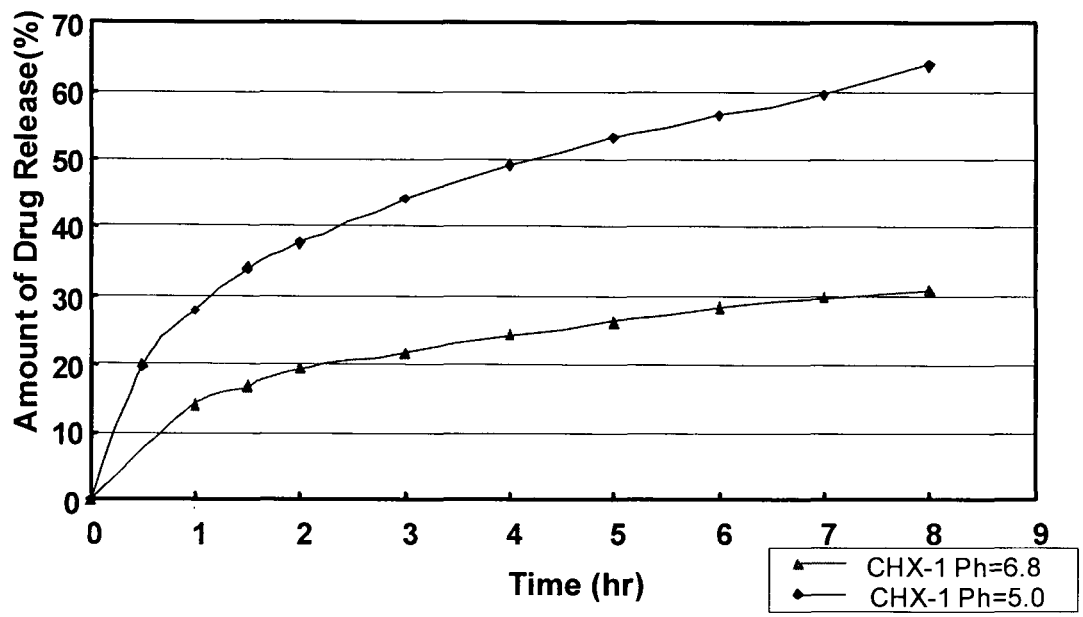

The released CHX concentration was measured spectrophotometrically at 260 nm (Uvikon 933: Kontron Instruments). The concentration of the CHX was calculated according to a reference curve. FIG. 3 shows the CHX release rate (as % of the initial amount in film) with time (from 1-8 hours) at two different pHs: 5.0 and 6.8, again showing a higher release rate at pH 5.0.

Figure 4:
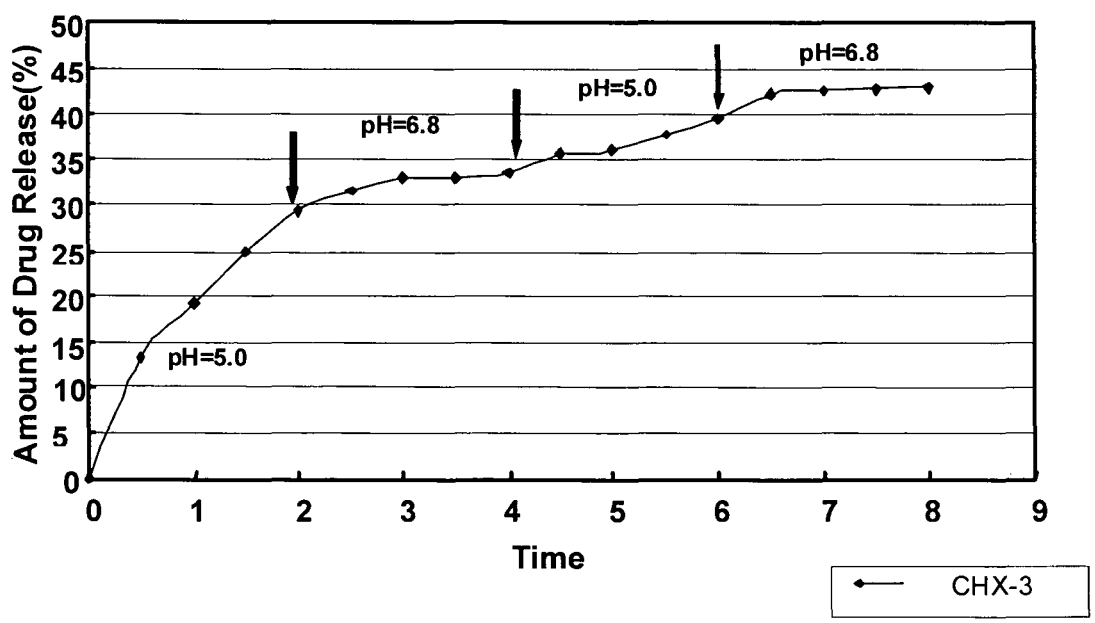

In a different experiment, the films were kept at a pH 5.0 buffer for 2 hours, then at a pH 6.8 buffer for 2 hours, then at a pH 5.0 buffer for 2 hours and again at a pH 6.8 buffer for 2 hours. Samples were taken at similar intervals. The results are shown in FIG. 4, which shows the CHX-1 release rate (as % of the initial amount in film) with time (1-8 hours), for this pH change profile. As shown at each sampling interval in FIG. 4, the release rate of CHX at pH 5.0 was faster than at pH 6.8, also demonstrating that pH of 6.8 retards the rate of release from the pH sensitive SRD.

Example 3: Preparation of pH-Sensitive Liquid Precursor Compositions Containing Triclosane, and Applications Thereof I. Preparation of Liquid Precursor Composition:

The liquid precursor composition was prepared as described in Example 1 (part I), replacing the clotrimazole by triclosane.-

II. Preparation of Film from the Liquid Precursor Composition:

The liquid precursor composition obtained in part I was poured (15 ml) on Teflon dishes (10.5 cm diameter) in a drying room and dried for about 4 hours. The obtained film was 0.177 mm thick.

Table 3 below shows the triclosane sample prepared, showing its composition both in the dry film and in the liquid precursor composition.

TABLE 3

| Formulation | Ingredient | % weight in dry film | % weight in liquid precursor composition |
|---|---|---|---|
| Triclosane-1 | Triclosane | 34.0 | 3.3 |
| | Ethyl Cellulose (EC) | 40.2 | 3.9 |
| | PEG 400 | 12.4 | 1.2 |
| | Eudragit E | 13.4 | 1.3 |
| | Ethanol | | 90.3 |

III. Determining the Release Rate of Triclosane from the Film of Part II:

Determining the triclosane release rate from the films was conducted by first placing the films in 100 ml glass vessels, containing Trizma base buffer (50 mM, +10% SLS (sodium lauryl sulphate) at pH=5.0 and 6.8 at 50 rpm, at 37° C.

Figure 5:
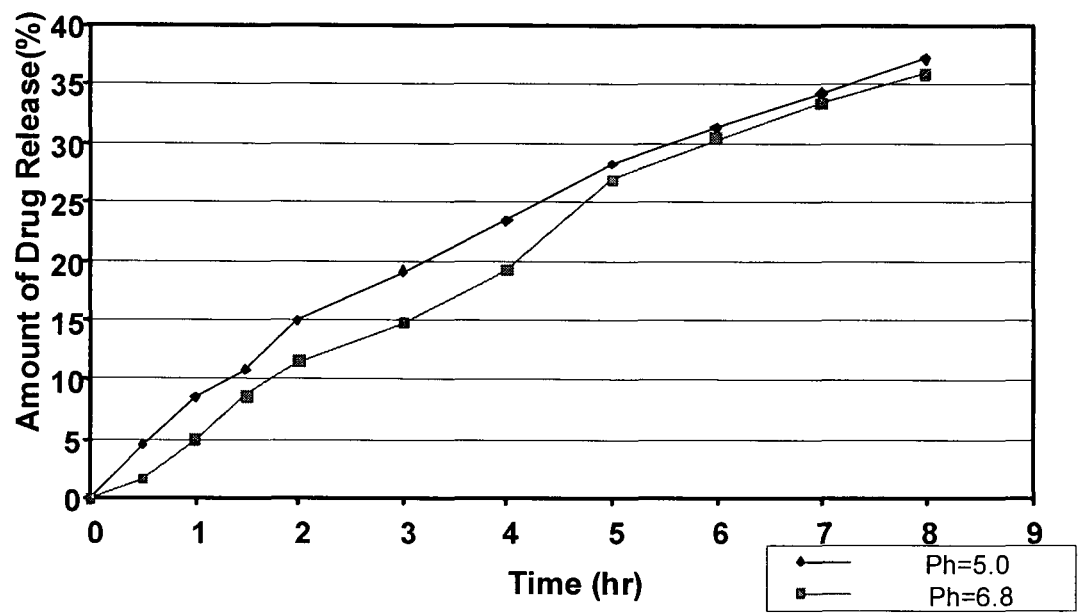

Then, 2 cc samples were taken from the glass vessels at pre-determined intervals (each hour from 1 to 8 hrs). The released triclosane concentration was measured spectrophotometrically at 280 nm (Uvikon 933: Kontron Instruments). The concentration of the triclosane was calculated according to a reference curve. FIG. 5 shows the triclosane (Tric-1) release rate as % of the initial amount in the film, with time (from 1-8 hours) at two different pHs: 5.0 and 6.8.

In a different experiment, the films were kept at a pH 5.0 buffer for 2 hours, then at a pH 6.8 buffer for 2 hours, then at a pH 5.0 buffer for 2 hours and again at a pH 6.8 buffer for 2 hours. Samples were taken at similar intervals. The results are shown in FIG. 6, which shows the Tric-1 release rate (as % of the initial amount in film) with time (1-8 hours), for this pH change profile.

Figure 6:
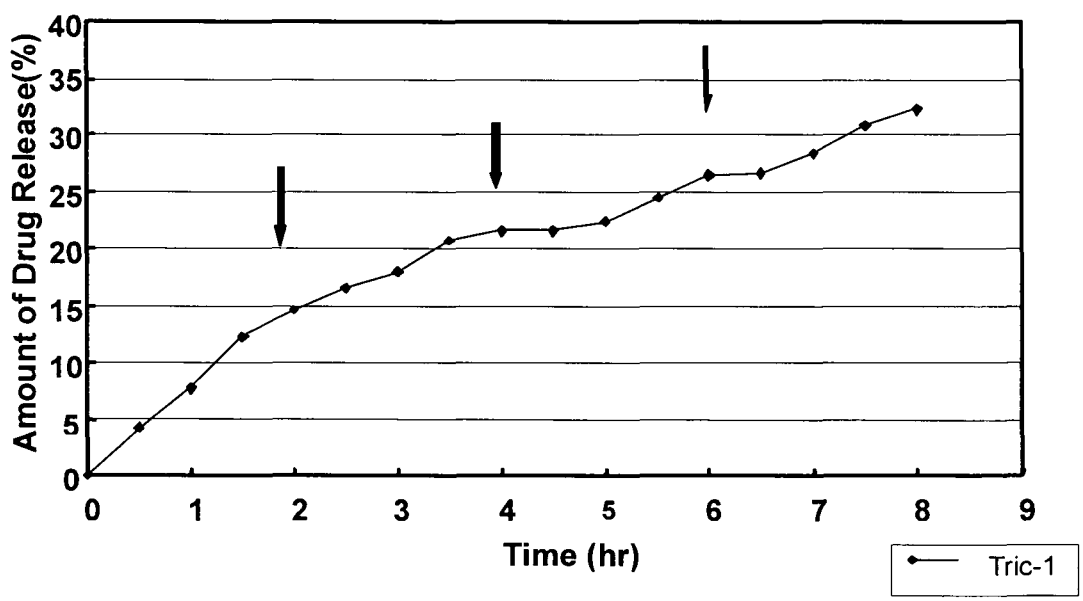

As shown at each sampling interval of FIG. 6, the release rate of triclosane at pH 5.0 was significantly faster than at pH 6.8.

Example 4: Preparation of pH Sensitive Liquid Precursor Compositions Containing Cetylpyridinium-Chloride (CPC), and Applications Thereof I. Preparation of Liquid Precursor Composition:

The liquid precursor composition was prepared as described in Example 1 (part I), replacing the clotrimazole by Cetylpyridinium-Chloride (CPC).

II. Preparation of Film from the Liquid Precursor Composition:

The liquid precursor composition obtained in part I was poured (15 ml) on Teflon dishes (10.5 cm diameter) in a drying room and dried for about 4 hours. The obtained film was 100-150 micron thick.

Table 4 below shows the triclosane sample prepared, showing its composition in the liquid precursor composition.

TABLE 4

| Ingredient | Sample CPC-1 | Sample CPC-2 | Sample CPC-3 |
|---|---|---|---|
| | % in liquid precursor formulation | | |
| Cetylpyridinum Chloride (CPC) | 10% | 15% | 20% |
| Ethyl Cellulose | 5% | 5% | 5% |
| Eudragit E | 1% | 2% | 3% |
| Triacetine (plasticizer) | 1% | 1% | 1% |
| Ethanol | 83% | 77% | 71% |

Example 5: Comparing the Antibacterial Activity of Samples with and without pH-Sensitive Polymers Ethyl-cellulose-based formulations with antimicrobial agents—Chlorhexidine (CHX) and Cetylpyridinium-Chloride (CPC) were prepared as detailed above in Examples 2 and 4, respectively either with the acidic pH sensitive polymer (Eudragit E) or without it. The duration of antibacterial bio-assay activity on S. mutans ATCC 27351 bacteria was tested by daily growth inhibition zone measurements around the formulations followed by transfer of the formulations to a newly plated agar media, until no inhibition was observed.

The compositions of the different tested liquid precursor compositions are given in Table 5 below.

TABLE 5

| Ingredient | formula 1: Controlled Release | formula 2: Placebo | formula 3: direct dripping on a Wattman paper |
|---|---|---|---|
| CHX (Active agent) | 2.5 grams (47.2% in dry film) | None | 0.07 gr |
| Ethyl cellulose | 1.74 gr (32.1% in dry film) | 1.74 gr | None |
| Eudragit E | 0.5 gr (9.4% in dry film) | 0.5 gr | None |
| PEG400 | 0.6 gr (11.3% in dry film) | 0.6 gr | None |
| Ethanol | 50 ml | 50 ml | 1.4 ml |

Results

Figure 7:
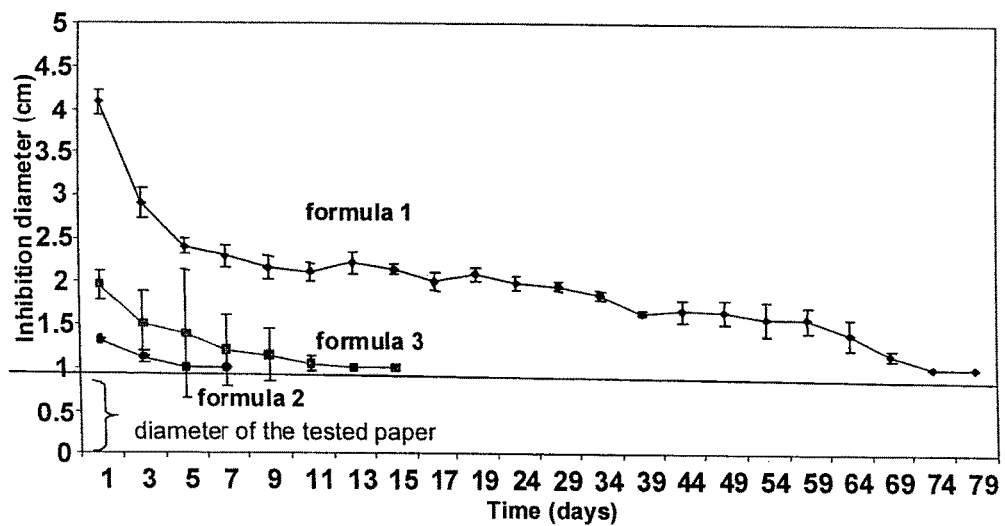

FIG. 7 shows the sustained antimicrobial activity on clinically isolated Streptococci by CHX formulations for formulas 1-3 detailed above, as a function of time (in days). As can be seen in FIG. 7, SRD containing CHX as an antimicrobial agent and a pH sensitive polymer Eudragit E exhibited the best prolonged antibacterial activity in-vitro, (for over 79 days) on S. mutans.

Example 6: Human Pharmacokinetics of the SRD Systems of the Present Invention

For clinical human pharmacokinetics trials, the liquid precursor compositions prepared according to Examples 1-4 (parts I, respectively) were prepared and used.

For example, clotrimazole slow-release acidic-pH sensitive formulation was prepared by dissolving 1.2 grams of clotrimazole, 0.9 grams of ethyl cellulose, 0.2 grams Eudragit E in 10 mL ethanol. The composition corresponds to the film dosage forms containing 30% of hydroxypropylcellulose. Oralten® troche (Agis Industries, Yeruham, Israel) containing 10 mg clotrimazole and 903.5 mg dextrose served as a commercial control.

The liquid precursor composition of the invention and the torch were applied to fourteen healthy volunteers. When studying the troche, the volunteers were asked to dissolve it in the mouth. On both sessions (liquid precursor composition of the invention or troches administration), an unstimulated saliva sample (2 ml in a calibrated tube) was collected 5 minutes before the application and at 5, 30, 60, 120, 180, 240 and 300 minutes after clotrimazole administration. The saliva samples were analyzed using HPLC. All pharmacokinetic and pharmacodynamic calculations were performed using WinNonlin® 5.0.1 software (Pharsight Corporation, Mountain View, Calif., USA). The area under the curve (AUC), terminal half-life and the time period above the minimally inhibitory concentration (T>MIC) for clotrimazole against *Candida albicans*, were determined from the concentration—time curves. All data is presented as the mean±SD. The between groups difference was assessed for statistical significance by the paired two-tailed Student's t-test.

The baseline saliva flow rate was very similar in both. The salivary flow rate for the first five minutes before application of the liquid precursor composition of the invention and troche administration was 3.9±2.5 ml and 4.3±2.0 ml, respectively. The amount of clotrimazole applied as liquid precursor composition of the invention was 9.21±2.27 mg (mean±SD), and the saliva concentration data was normalized to allow comparison with 10 mg troche.

Figure 8:
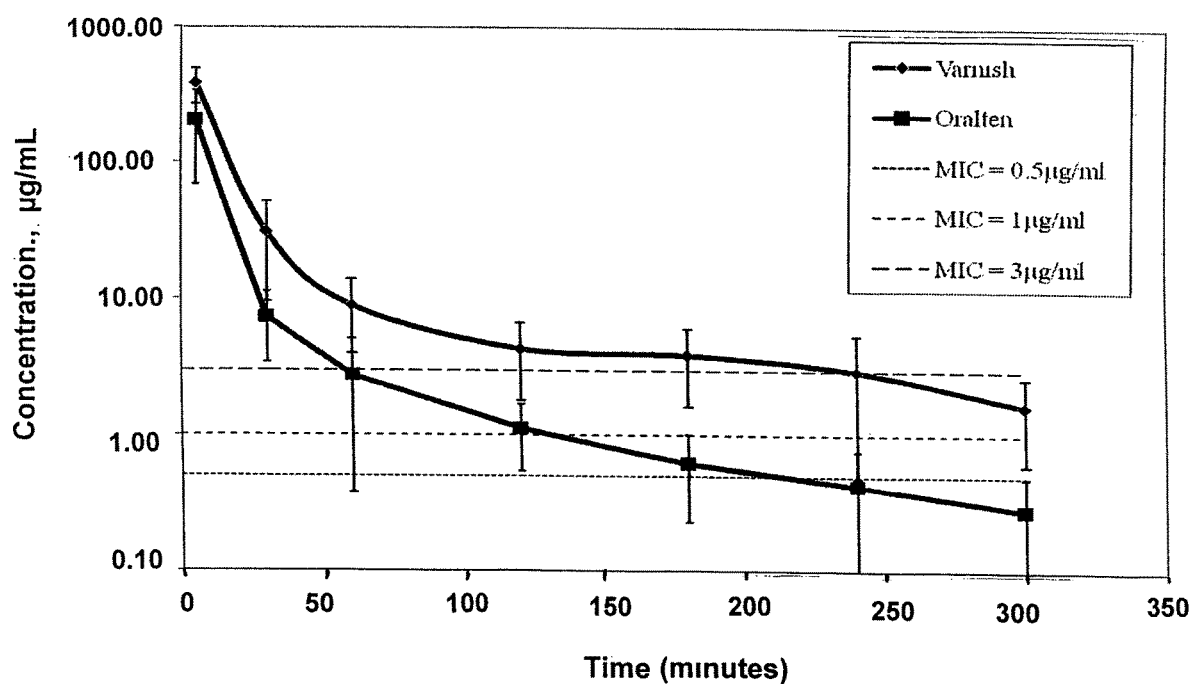

FIG. 8 shows the clotrimazole concentration in saliva (mean±SD) at different time intervals (minutes) following drug administrations, both according to preferred embodiments of the invention (termed "Varnish" in the figure) and for a control troche composition (termed "Oralten" in the figure). As can be seen from this figure, at all time points salivary clotrimazole concentrations were higher in the liquid precursor composition group than in the troche group. The initial (up to ~60 minutes) very rapid decline in concentration was observed in both groups and it was followed by a under the much slower elimination phase. The terminal phases of the kinetic rates were significantly different between the two groups. During the experiment, the liquid precursor composition of the invention group showed an area curve ($AUC_{0\to 300}$), which was more than double that of the troche group (p<0.001).

Pharmacodynamics:

The pharmacodynamic comparison of the two formulations can be simulated by calculating time over minimal inhibiting concentrations (MIC) of clotrimazole that was obtained in saliva. The concentrations the clotrimazole from the liquid precursor were above typical MIC values (0.5-3 mg/ml) and its duration above the MIC are extended compared to the troche group. E.g. 60 minutes duration of clotrimazole at the therapeutic window for the torch compared to 240 minutes for the liquid precursor at MIC 3 mg/ml. Thus, the time over MIC following application of the liquid precursor composition of the invention was more than 3-fold longer than following administration of the troche.

The invention claimed is:

1. A liquid precursor composition adapted for application on a hard surface in the oral cavity, to form a film thereon that releases a therapeutic agent at a first rate when in an acidic environment with a pH below 6.0 and at a second rate that is lower than the first rate when in a normal pH of 7.2-6.8, said composition comprising a mixture of:
    a. at least one therapeutic agent suitable for the treatment of oral disorders,
    b. at least one acidic-pH sensitive polymer having enhanced degradation below pH 6.0, said polymer having primary, secondary or tertiary amino groups,
    c. at least one hydrophobic polymer insoluble in saliva, and
    d. a pharmaceutically acceptable volatile carrier,
    wherein the weight ratio between said at least one hydrophobic polymer and said at least one acidic-pH sensitive polymer is about 1.5:1 to about 5:1,
    wherein the composition has the property that, upon application onto a hard surface, a film having a thickness range from about 30 microns to about 150 microns is formed containing the at least one hydrophobic polymer, within which is embedded the at least one acidic-pH sensitive polymer and the at least one therapeutic agent, from which the therapeutic agent will be released at a first rate when in an acidic environment with a pH below 6.0 and at a second rate that is lower than the first rate when in a normal pH of 7.2-6.8.

2. The composition of claim 1, wherein said hydrophobic polymer is selected from the group consisting of: copolymer hydrogels of hydroxymethyl methacrylate (HEMA) and methylmethacrylate (MMA), poly(acrylic acid), poly(m-ethyl vinyl ether co-maleic anhydride), poly(ethylene oxide), karya gum, poly (hydroxyethylmethacrylate), ethyl cellulose (EC), silicone rubber, polyethylene, polylactic acid, polymethylmethacrylate, polyvinyl chloride, polyvinyl acetate, and polyurethane.

3. The composition of claim 1, wherein said therapeutic agent is selected from the group consisting of an antibiotic agent, an antibacterial agent, an antiseptic agent, an antifungal agent, an anti-viral agent, a bone and/or tissue growth factor agent, an anti tumor agent, an anti-inflammatory agent, an anti mal-odor agent, a tooth whitening agent, a bleaching agent, a dental hypersensitivity agent, a plaque treatment agent, dry mouth treatment agent, a biofilm treatment agent, a caries treatment agent, a periodontal diseases treatment agent, a gingivitis treatment agent, a tooth staining treatment agent, an aphthous or ulcer treatment agent, an anti protozoa agent and a stomatitis agent.

4. The composition of claim 3, wherein said therapeutic agent is selected from the group consisting of triclosane, chlorhexidinediacetate (CHX), clotrimazole and cetylpyridium-chloride (CPC).

5. The composition of claim 1, wherein said acidic-pH sensitive polymer is dimethylaminoethyl methacrylate copolymer.

6. The composition of claim 1, wherein the weight ratio between said at least one hydrophobic polymer and said at least one acidic-pH sensitive polymer is from 2:1 to 3:1.

7. The composition of claim 5, wherein the hydrophobic polymer is ethyl cellulose.

8. The composition of claim 7, wherein the weight ratio between the ethyl cellulose and dimethylaminoethyl methacrylate copolymer is from 2:1 to 3:1.

9. A liquid precursor composition according to claim 1, wherein the weight ratio between the hydrophobic polymer and the acidic-pH sensitive polymer is from 2:1 to about 5.1.

10. A method for treating, preventing, ameliorating or eliminating at least one oral disorder, said method comprising topically applying the liquid precursor compositions of claim 1 to a hard surface in the oral cavity or on a hard surface to be placed in the oral cavity, allowing said composition to solidify, thereby forming a film on said hard surface.

* * * * *